(12) United States Patent
Park et al.

(10) Patent No.: US 11,448,936 B2
(45) Date of Patent: Sep. 20, 2022

(54) ELECTROCHROMIC STRUCTURE AND PREPARATION METHOD THEREFOR

(71) Applicant: LG ELECTRONICS INC., Seoul (KR)

(72) Inventors: Koun Park, Seoul (KR); Sangmo Koo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 188 days.

(21) Appl. No.: 16/332,699

(22) PCT Filed: Dec. 14, 2016

(86) PCT No.: PCT/KR2016/014661
§ 371 (c)(1),
(2) Date: Mar. 12, 2019

(87) PCT Pub. No.: WO2018/052169
PCT Pub. Date: Mar. 22, 2018

(65) Prior Publication Data
US 2019/0361308 A1 Nov. 28, 2019

(30) Foreign Application Priority Data
Sep. 13, 2016 (KR) .......... 10-2016-0118283

(51) Int. Cl.
*G02F 1/155* (2006.01)
*G02F 1/153* (2006.01)
(Continued)

(52) U.S. Cl.
CPC .......... *G02F 1/1533* (2013.01); *G02F 1/163* (2013.01); *B82Y 20/00* (2013.01)

(58) Field of Classification Search
CPC .......... G02F 1/15; G02F 1/1533; G02F 1/155; G02F 1/1514; G02F 1/163; G02F 1/153;
(Continued)

(56) References Cited

U.S. PATENT DOCUMENTS 7,532,383 B2 * 5/2009 Jang .......................... G02F 1/15
359/266
8,593,715 B2 * 11/2013 Yashiro ................ C07D 213/57
359/273
(Continued)

FOREIGN PATENT DOCUMENTS

KR  10-2009-0105794 A  10/2009
KR  10-2010-0020417 A   2/2010
(Continued)

OTHER PUBLICATIONS

Kim et al., "Nanoporous Metal Oxides with Tunable and Nanocrystalline Frameworks via Conversion of Metal-Organic Frameworks", Journal of the American Chemical Society, vol. 135, 2013, p. 8940-8946.

*Primary Examiner* — Audrey Y Chang
(74) *Attorney, Agent, or Firm* — Birch, Stewart, Kolasch & Birch, LLP

(57) ABSTRACT

The present invention relates to a nanostructure having an electrochromic material attached to the surface thereof, and a preparation method therefor. To this end, the present invention provides: a nanostructure comprising a metal oxide and having a structure comprising nanopores; and an electrochromic structure comprising an electrochromic material to be attached to the surface of the nanostructure. According to the present invention, the nanostructure has a surface area larger than that of conventional nanoparticles so as to enable more electrochromic materials to be attached (Continued)

thereto, and thus the electrochromic characteristics of an electrochromic device can be improved.

14 Claims, 5 Drawing Sheets

(51) Int. Cl.
 *G02F 1/163* (2006.01)
 *B82Y 20/00* (2011.01)
(58) Field of Classification Search
 CPC ...... B82Y 20/00; B82Y 40/00; C07D 401/04; C07D 333/24; C07D 213/57; C09K 9/02; C07C 69/82
 USPC ........... 359/273, 266, 265, 268, 275; 345/49
 See application file for complete search history.

(56) References Cited

U.S. PATENT DOCUMENTS

| 8,970,937 | B2* | 3/2015 | Son | C07D 333/24 |
| | | | | 359/265 |
| 2006/0203535 | A1 | 9/2006 | Ishii et al. | |
| 2007/0171148 | A1* | 7/2007 | Cassidy | G02F 1/163 |
| | | | | 345/49 |
| 2011/0043886 | A1* | 2/2011 | Jeon | G02F 1/155 |
| | | | | 359/273 |
| 2012/0139824 | A1* | 6/2012 | Takahashi | G02F 1/155 |
| | | | | 345/105 |
| 2014/0327950 | A1* | 11/2014 | Trajkovska-Broach | G02F 1/1524 |
| | | | | 359/265 |
| 2015/0185580 | A1* | 7/2015 | Cho | G02F 1/153 |
| | | | | 359/266 |
| 2015/0331295 | A1* | 11/2015 | Takahashi | G02F 1/1524 |
| | | | | 359/275 |
| 2016/0033839 | A1* | 2/2016 | Lee | C09K 9/02 |
| | | | | 359/268 |
| 2016/0216588 | A1* | 7/2016 | Ah | G02F 1/155 |

FOREIGN PATENT DOCUMENTS

| KR | 10-2011-0020436 A | 3/2011 |
| KR | 10-2011-0106622 A | 9/2011 |

* cited by examiner

ELECTROCHROMIC STRUCTURE AND PREPARATION METHOD THEREFOR

CROSS REFERENCE TO RELATED APPLICATIONS

This application is the National Phase of PCT International Application No. PCT/KR2016/014661, filed on Dec. 14, 2016, which claims priority under 35 U.S.C. 119(a) to Patent Application No. 10-2016-0118283, filed in Republic of Korea on Sep. 13, 2016, all of which are hereby expressly incorporated by reference into the present application.

TECHNICAL FIELD

The present invention relates to a nanostructure having an electrochromic material attached to the surface thereof, and a preparation method therefor.

BACKGROUND ART

Electrochromism is a phenomenon in which coloration or decolorization is performed by electrochemical oxidation or reduction reaction depending on the direction of application of electric current. An electrochromic material maintains a predetermined color, and when electric current is applied, the electrochromic material will be discolored to another color. And, when the direction of the electric current is reversed, the original color of the electrochromic material is restored.

Here, the absorption spectrum of the electrochromic material is changed by oxidation or reduction reaction. That is, the electrochromic material does not emit light by itself, but takes on a color through light absorption. Electrochromic devices having these properties have been widely used for uses such as mirrors and sunroofs for vehicles, smart windows, and outdoor displays.

Meanwhile, electrochromic materials are classified into a memory type in which once the discoloration occurs, the discolored state is maintained even though no voltage is applied between an upper electrode and a lower electrode, and a non-memory type in which even though discoloration occurs, the discolored state is maintained only when voltage is continuously applied between the upper electrode and the lower electrode.

The memory type has a very high utilization value because the power consumption for the material discoloration is not high. Thus, various studies for utilizing the memory type electrochromic material have been conducted.

However, an electrochromic material in the related art has disadvantages in that it is difficult to implement various colors, and to implement high shielding properties because only one material takes part in discoloration. Further, the electrochromic matter in the related art has a disadvantage in that it is difficult to simultaneously implement a high discoloration speed and high light-shielding properties.

Meanwhile, in the related art, an electrochromic material is attached to the surface of nanoparticle, and is utilized in an electrochromic device. In this case, studies for increasing the electrochromic speed by improving the efficiency and speed of electronic transition between nanoparticles have been conducted.

DISCLOSURE OF THE INVENTION

Therefore, an object of the present invention is to provide an electrochromic substance having an improved discoloration property by attaching an electrochromic material to a porous nanostructure.

Further, another object of the present invention is to provide a method for selectively attaching a nanostructure electrochromic material by controlling the size and number of pores included in a porous nanostructure.

To achieve these and other advantages and in accordance with the purpose of the present invention, as embodied and broadly described herein, there is provided a nanostructure comprising a metal oxide and having a structure comprising nanopores; and an electrochromic structure comprising an electrochromic material to be attached to the surface of the nanostructure.

In an Example, the pores are characterized by including first pores having a diameter within a predetermined range and second pores having a diameter within a range different from the predetermined range, and a first electrochromic material may be attached to a surface corresponding to the first pores and a second electrochromic material may be attached to a surface corresponding to the second pores. Through this, the present invention may adjust the ratio of different types of electrochromic materials attached to a nanostructure by adjusting the number of pores having different diameters to be formed in the nanostructure.

In an Example, the diameters of the second pores are characterized by being larger than those of the first pores, and the second electrochromic material may have a molecular weight higher than that of the first electrochromic material. Through this, the present invention may selectively attach an electrochromic material to specific pores by adjusting the molecular size of the electrochromic material.

In an Example, the nanostructure is characterized by being composed of a plurality of layers, and diameters of pores included in one layer in the layers and diameters of pores included in the other layer in the layers may be different from each other. Through this, different electrochromic materials may be attached to each of the layers included in the nanostructure.

In an Example, the one layer may be laminated and formed on the other layer. Through this, the present invention enables different electrochromic materials to be overlapped with each other and become electrochromic.

In an Example, the one layer and the other layer may be disposed in parallel. Through this, the present invention enables different electrochromic materials to be uniformly electrochromic and simultaneously take on an inherent color of each of the electrochromic materials.

Further, the present invention provides a method for preparing an electrochromic nanostructure, the method including: preparing a metal organic framework having a predetermined size; preparing a nanostructure having a structure comprising nanopores by heat-treating the metal organic framework having a predetermined size; and attaching an electrochromic material to the surface of the nanostructure by immersing the nanostructure in a solution of the electrochromic material.

According to the present invention, the nanostructure has a surface area larger than that of conventional nanoparticles so as to enable more electrochromic materials to be attached thereto, and thus the electrochromic characteristics of an electrochromic device can be improved.

Further, according to the present invention, the electron transfer speed for an electrochromic material may be increased, so that a discoloration speed of an electrochromic device may be improved.

In addition, unlike conventional core-shells in the related art, which are discolored by electron hoping of nanoparticles, the electrochromic structure according to the present invention enables an electrochromic material attached to the nanostructure to be uniformly reduced or oxidized through a porous nanostructure.

MODES FOR CARRYING OUT THE PREFERRED EMBODIMENTS

Reference will now be made in detail to the preferred embodiments of the present invention, examples of which are illustrated in the accompanying drawings. It will also be apparent to those skilled in the art that various modifications and variations can be made in the present invention without departing from the spirit or scope of the invention. Thus, it is intended that the present invention cover modifications and variations of this invention provided they come within the scope of the appended claims and their equivalents.

Description will now be given in detail of a drain device and a refrigerator having the same according to an embodiment, with reference to the accompanying drawings.

An electrochromic structural body according to the present invention is utilized in an electrochromic device. Hereinafter, an electrochromic device will be described before describing an electrochromic structural body.

Figure 1:
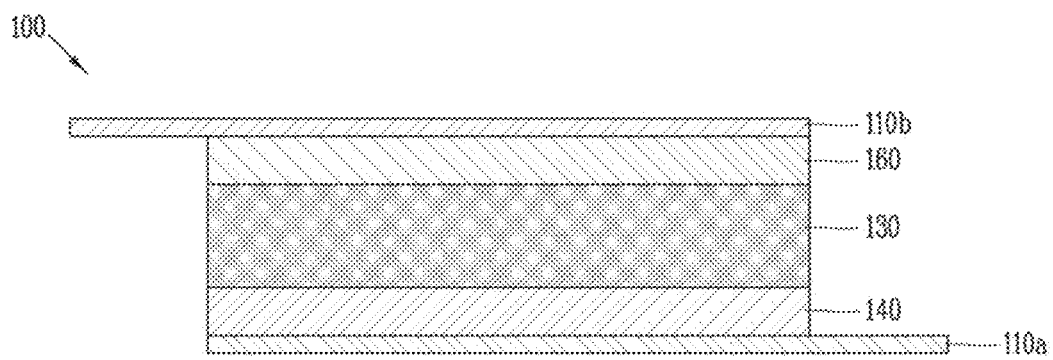
FIG. 1 is a conceptual view illustrating an electrochromic device.

FIG. 1 is a conceptual view illustrating an electrochromic device.

An electrochromic device 100 includes an electrolyte layer 130, an electrochromic layer 140, and an ion storage layer 160 between a first transparent electrode 110a and a second transparent electrode 110b facing the first transparent electrode 110a. Hereinafter, a transparent electrode and constituent elements included between the two transparent electrodes will be described in detail with reference to FIG. 1. Meanwhile, the electrochromic device may not include some of the above-described constituent elements, or may further include other constituent elements.

The first and second transparent electrodes 110a and 110b are electrodes having optical transparency and conductivity. The transparent electrode may be formed on a substrate formed of glass or a light-transmitting film, and may be a thin film formed of tin oxide, indium oxide, platinum, and gold, or a thin film formed of a conductive polymer.

The transparent electrode is used to apply voltage to an electrochromic material, and a power supply device is connected to one end of the transparent electrode. The power supply device generates a potential difference between two transparent electrodes facing each other.

In the electrochromic device, the first and second transparent electrodes have a predetermined area, and at least a part of an upper surface of the first transparent electrode 110a and at least a part of a lower surface of the second transparent electrode 110b face each other.

The transparent electrode transfers electric charge to an electrochromic material positioned between the transparent electrodes, so that the electrochromic material is oxidized or reduced.

When voltage is applied between the first and second transparent electrodes, the electrolyte layer 130 transfers the electric charge between the two electrodes to the electrochromic layer 140, and may be formed of a liquid-phase, quasi solid-phase, or solid-phase electrolyte.

Meanwhile, the electrolyte layer 130 may be positioned between the first bus electrode 120 and the second transparent electrode 110b. Here, the electrolyte layer 130 does not come in contact with the first bus electrode 120, and the electrochromic layer 140 may be formed in a space formed between the electrolyte layer 130 and the first bus electrode 120.

Further, the electrolyte layer 130 may or may not come in contact with the second transparent electrode 110b. When the electrolyte layer 130 does not come in contact with the second transparent electrode 110b, another layer may be positioned between the electrolyte layer 130 and the second transparent electrode 110b. This will be described below.

The electrochromic layer 140 may be formed of an electrochromic material. The electrochromic layer 140 may be formed of an electrochromic material structural body according to the present invention. The electrochromic material constituting the first electrochromic layer 140 is not limited to a specific material, and may be any material which is oxidized or reduced between the first and second transparent electrodes and may be discolored.

The electrochromic layer 140 is positioned between the first transparent electrode 110a and the electrolyte layer 130, and comes in contact with the electrolyte layer 130. The electrolyte layer 130 allows the electrochromic material included in the electrochromic layer 140 to be oxidized or reduced by transferring electric charge to the electrochromic layer 140 and the nanostructure 200 is included in the electrochromic layer 140 (e.g., see FIGS. 2, 5A and 5B).

The ion storage layer 160 serves to strengthen the charge transferring power of the electrochromic device, and may be formed of a highly ion conductive inorganic material such as antimony-doped tin oxide. The ion storage layer 160 may be positioned between the second transparent electrode 110b and the electrolyte layer 130, and may come in contact with the second transparent electrode 110b and the electrolyte layer 130.

As described above, the electrochromic device induces charge transfer to the electrochromic layer and oxidizes or reduces the electrochromic material included in the electrochromic layer. In this case, electric charge is transferred through electrons. Accordingly, the electron transfer rate in the electrochromic layer and the electrochromic rate of the electrochromic device are greatly affected.

An electrochromic structure according to the present invention improves an electrochromic speed of an electrochromic device by improving the electronic transition speed.

Further, the structure according to the present invention has a high surface area, and thus may attach a large amount of electrochromic material, and when the structure according to the present invention is utilized, an electrochromic device having a desired color may be implemented even though the structure according to the present invention has a small thickness.

Hereinafter, the electrochromic structure according to the present invention will be described.

Figure 2:
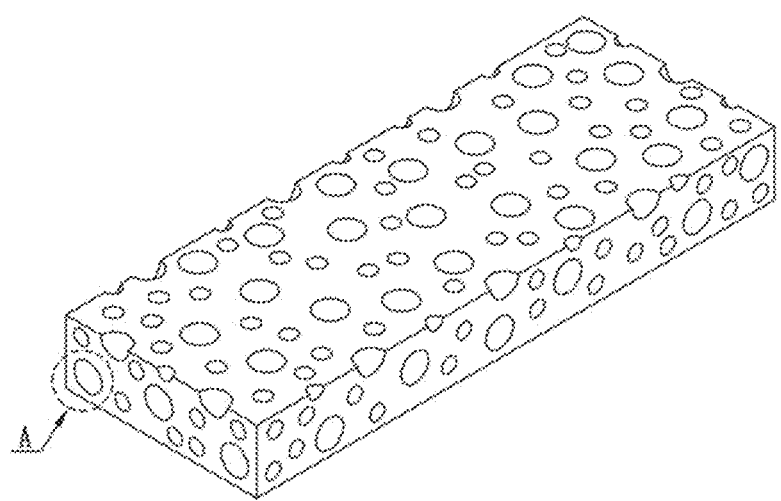
FIG. 2 is a conceptual view illustrating an electrochromic structure according to the present invention.
Figure 3:
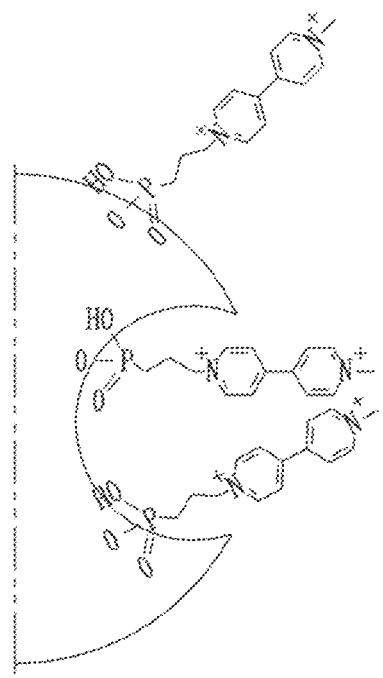
FIG. 3 is an enlarged view which enlarges A in FIG. 2.

FIG. 2 is a conceptual view illustrating an electrochromic structure according to the present invention, and FIG. 3 is an enlarged view which enlarges A in FIG. 2.

The electrochromic structure according to the present invention includes a nano structure having a porous structure and an electrochromic material attached to the surface of the nanostructure.

Referring to FIG. 2, the nanostructure includes a metal oxide and has a structure comprising nanopores. The nanostructure has a large surface area due to a plurality of pores included in the nanostructure. The pores included in the nanostructure have a diameter ranging from several nanometers to several hundred nanometers.

In the present specification, the surface of the nanostructure is not only a concept including an outer surface of the nanostructure, but also a concept including a surface which divides the pore included in the inside of the nanostructure.

Meanwhile, in the present specification, when specifying the surface, which divides a specific pore in pores having different sizes, an expression "a surface corresponding to a pore" is used. For example, in the present specification, a surface, which divides pores having a first average diameter, is expressed as a surface corresponding to pores having a first average diameter.

Meanwhile, a metal oxide constituting a nanostructure may be formed of at least one of tungsten oxide, molybdenum oxide, tantalum oxide, niobium oxide, vanadium oxide, iron oxide, tin oxide, bismuth oxide, cerium oxide, manganese oxide, chromium oxide, cobalt oxide, rhodium oxide, iridium oxide, and nickel oxide.

Meanwhile, in the present invention, since a pore included in the nanostructure is not perfectly spherical, the size of a pore is expressed as an average diameter of pores. That is, in the present specification, "the diameter of a pore" means "an average diameter of pores".

Meanwhile, in general, it is difficult for the diameters of pores included in one nanostructure to be perfectly the same as each other. Thus, in the present invention, pores having diameter within a predetermined diameter range are classified into the same group. Meanwhile, in the present specification, the pores classified into the same group may be expressed as "first pores", "second pores", and the like.

The nanostructure according to the present invention may include only pores belonging to the same group, and may include pores classified into a plurality of different groups. For example, one nanostructure may include first pores and second pores. Meanwhile, the pore group included in one nanostructure is not limited to the two kinds.

Meanwhile, when the nanostructure includes pores classified into a plurality of different groups, the pores included in the nanostructure may be arranged in various ways in the nanostructure.

For example, the nanostructure may be composed of a single layer, and when a nanostructure composed of a single layer includes first and second pores, each of the first and second pores is unevenly distributed in a portion of the nanostructure, and may have a uniform distribution.

For another example, the nanostructure may include a plurality of layers, and pores in different groups may be disposed in each layer.

Specifically, the one layer may be laminated and formed on the other layer. Through this, the present invention enables different electrochromic materials to be overlapped with each other and become electrochromic.

Meanwhile, the one layer and the other layer may be disposed in parallel. Through this, the present invention enables different electrochromic materials to be uniformly electrochromic and simultaneously take on an inherent color of each of the electrochromic materials.

The placement of the pores included in the nanostructure has an important influence on the electrochromic characteristics of the electrochromic structure according to the present invention. The present invention adjusts the size, number, arrangement method, and the like of pores included in the nanostructure during the process of preparing the nanostructure. This will be described below.

Meanwhile, electrochromic materials may be attached to the surface of the above-described nanostructure.

In the present specification, the attachment means a state where an electrochromic material is fixed to the surface of the nanostructure by a chemical or physical bond between the nanostructure and the electrochromic material.

The nanostructure according to the present invention serves as an electron transfer medium for allowing an electrochromic material to be oxidized or reduced. That is, the electrochromic material may be attached to the nanostructure to transfer electrons to the nanostructure or accept electrons from the nanostructure.

In the related art, an electrochromic material having a nano core-shell structure is oxidized or reduced by electron hopping of nanoparticles. By this method, electrochromic materials included in an electrochromic device may not become uniformly electrochromic.

In contrast, the nanostructure according to the present invention allows electrons for the electrochromic material attached to the surface thereof to be uniformly transferred, thereby enabling uniform electrochromism.

The electrochromic material may be an organic material, and may have different colors, molecular sizes, and molecular weights depending on the type thereof.

For example, the following Chemical Formulae 1 to 3 are electrochromic materials which may be attached to the surface of the nanostructure, and take on a color of blue, red, and green, respectively, when the electrochromic material becomes electrochromic. Further, molecules represented by the following Chemical Formulae 1 to 3 have different molecular weights and molecular sizes. The following materials corresponding to the colors of blue, red, and green are only an Example, and the electrochromic materials having different molecular weights and molecular sizes may be attached to the surface of the nanostructure irrespective of the type thereof.

[Chemical Formula 1]

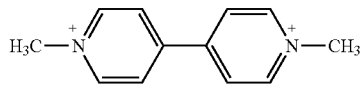

[Chemical Formula 2]

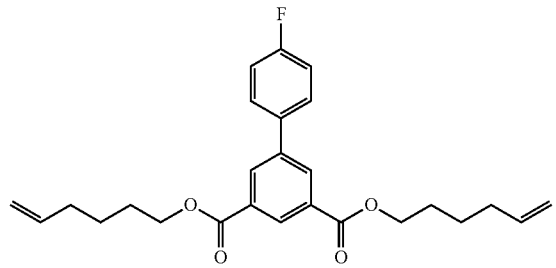

[Chemical Formula 3]

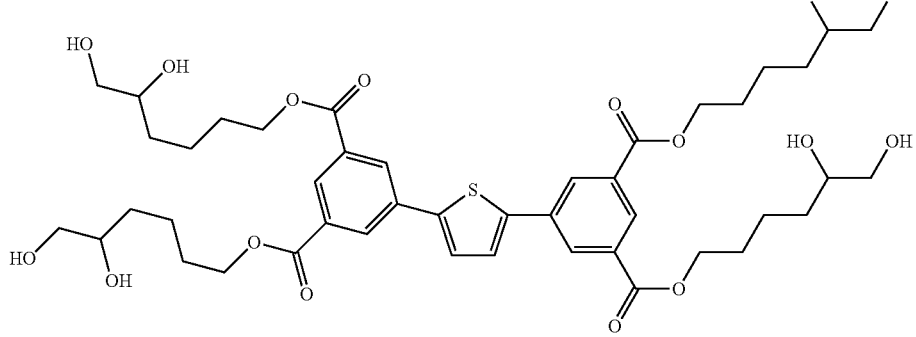

Meanwhile, the electrochromic material may be a polymer compound. Specifically, the polymer compound may be any one of polythiophene, poly(3-methylthiophene), polypyrrole, poly(3-methylketopyrrole), poly(3,4-dimethylpyrrole), poly(N-methylpyrrole), polyaniline, poly(2-methylaniline), and poly(3-methylaniline).

Meanwhile, the electrochromic material may be easily attached to the surface of the nanostructure by substituting the end of the electrochromic material with a —COOH group, a —OH group, a —PO$_3$H$_2$ group, or the like. For example, referring to FIG. 3, the end of the electrochromic material represented by Chemical Formula 1 is substituted with a —PO$_3$H$_2$ group, and then the electrochromic material may be adsorbed onto the surface of the nanostructure.

Meanwhile, since molecules having a diameter larger than a diameter of a specific pore included in the nanostructure cannot enter pores, the molecules cannot be attached to the pores. When this is utilized, in attaching different types of electrochromic materials to a single nanostructure, the ratio of electrochromic materials to be attached may be adjusted.

For example, when the molecules represented by Chemical Formulae 1 and 3 are attached to the nanostructure, the molecular size may be increased by substituting the end of the molecule represented by Chemical Formula 3 with an alkyl group. In this case, the selectivity for pores of the electrochromic material may be increased.

Hereinafter, a method for controlling a pore size distribution of a nanostructure and a method for attaching an electrochromic material will be specifically described while describing a method for preparing the above-described electrochromic structure.

Figure 4:
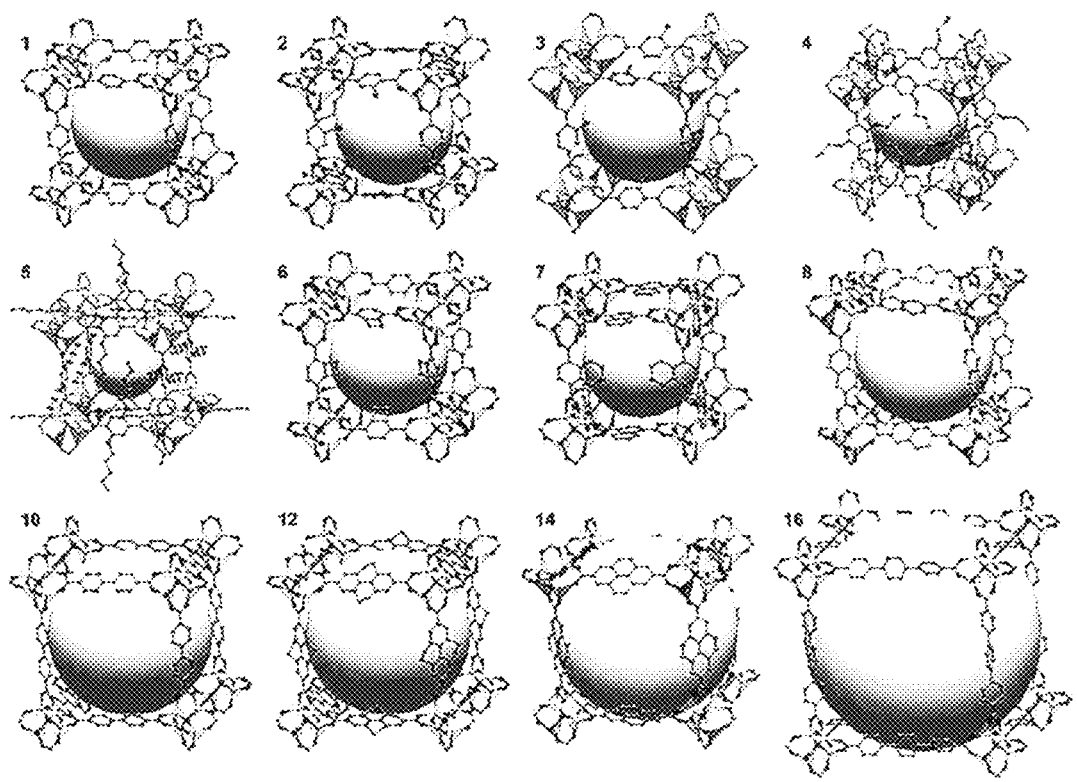
FIG. 4 is a conceptual view illustrating metal organic frameworks having different sizes.
Figure 5A:
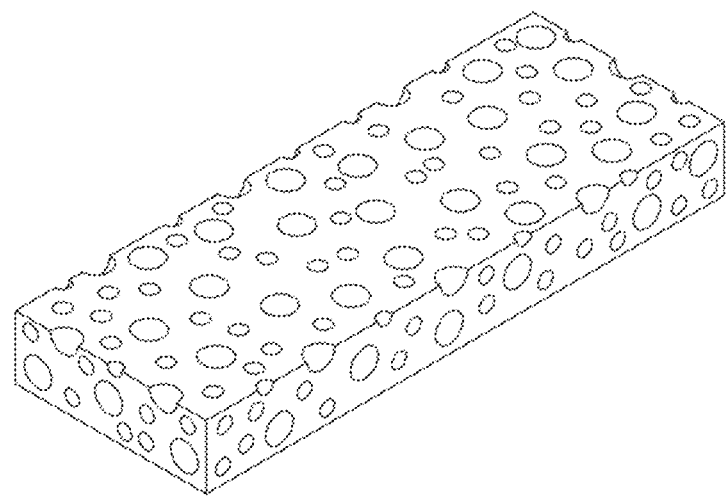
FIGS. 5A to 5C are conceptual views illustrating a nanostructure according to the present invention.
Figure 5B:
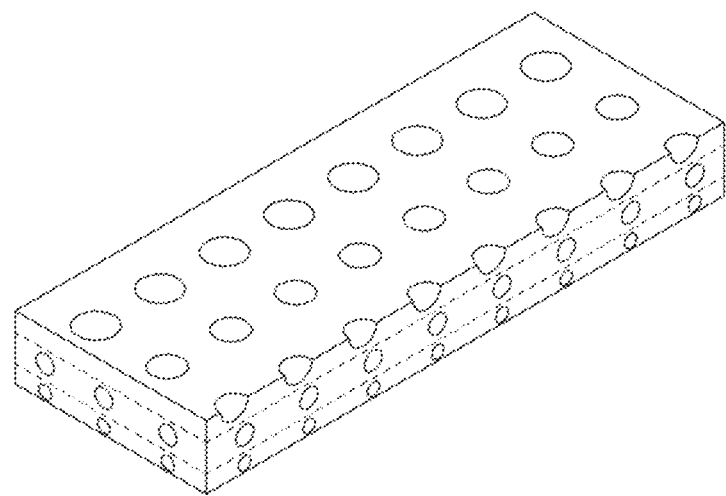
Figure 5C:
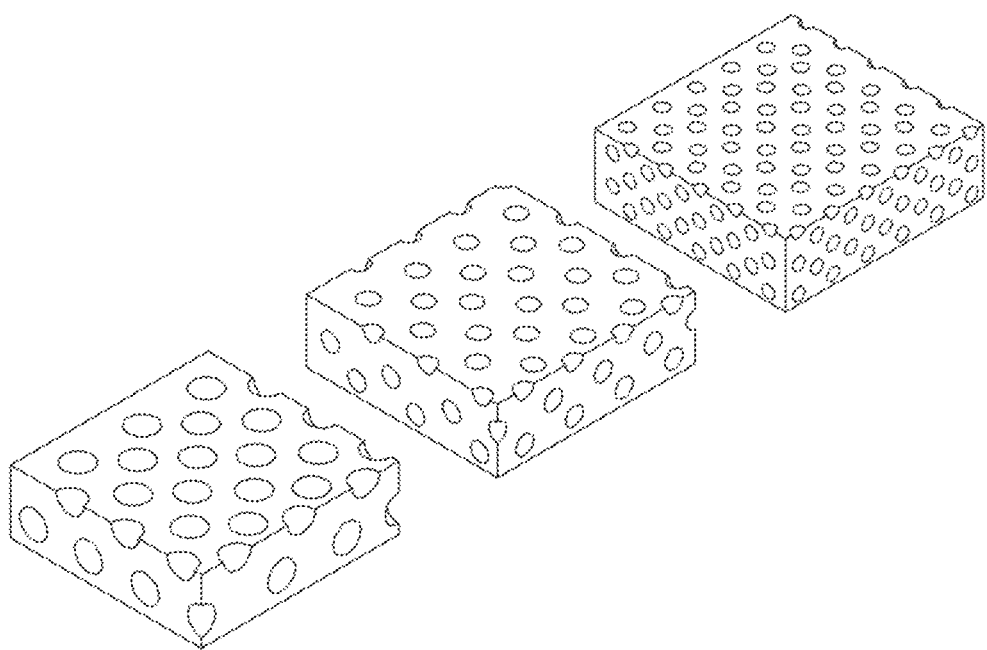

FIG. 4 is a conceptual view illustrating metal organic frameworks having different sizes, and FIGS. 5A to 5C are conceptual views illustrating a nanostructure according to the present invention.

First, in the present invention, a step of preparing a metal organic framework (MOF) is performed.

The MOF is formed of a metal or metal cluster and a linker. Here, the linker is a ligand which is bonded to the metal or metal cluster. The ligands may form various structures through a crosslinking, and in this case, what serves as a template is the metal or metal cluster.

MOFs having various pore sizes and shapes may be synthesized by varying the type of ligand. As the ligand, it is possible to use at least one of oxalic acid, malonic acid, succinic acid, glutaric acid, phthalic acid, isophthalic acid, terephthalic acid, biphenyl-4,4'-dicarboxylic acid, citric acid, trimesic acid, 1,2,3-triazole, pyrrodiazole, and squaric acid, and all the ligands which may be bonded to the metal may be used without being limited thereto.

The MOF may be prepared by mixing a metal oxide and a ligand at a constant ratio, and then carrying out a heat treatment such that the ligand forms crystals in a constant form with the metal oxide. In this case, the heat treatment needs to be carried out at a temperature at which the ligand itself is not decomposed.

Meanwhile, an MOF which uses a specific metal as a template may be prepared under a solvent-free condition. Specifically, metal acetate and an organic ligand are mixed and ground with a ball mill. Through this, the MOF may be rapidly synthesized.

Meanwhile, the MOF may be synthesized by a chemical vapor deposition method. Specifically, a metal oxide precursor film is formed. Thereafter, a phase transition to MOF crystals is induced by exposing the precursor film to ligand molecules.

As in FIG. 4, MOFs having different sizes may be synthesized by varying the type of metal and the type of ligand, which are used in the synthesis of the MOF.

Thereafter, a step of preparing a nanostructure having a structure including nanopores is performed by heat-treating the synthesized MOF.

When an MOF prepared by the above-described method is used, a nanostructure in the form of a membrane or in the form of a powder may be prepared. In this case, the powder form may be spherical, tetrahedral, hexahedral, rod-like, and the like.

Taking the case of preparing a nanostructure in the form of a membrane using an MOF as an example, when the prepared MOF is applied on a predetermined substrate and then heat-treated, the MOFs aggregate with each other, and as a result, a structure in the form of a membrane is formed. Here, the MOF may be applied in the form of a powder or a solution on a substrate.

Meanwhile, when the MOF is heat-treated, it is possible to help pores to be formed by continuously supplying a nitrogen gas having low reactivity.

Meanwhile, a nanostructure may be prepared by mixing MOFs having different sizes. Here, the MOFs having different sizes are mixed at a predetermined ratio, and the size distribution of the pores included in the nanostructure varies depending on the predetermined ratio.

For example, when a first MOF is heat-treated, pores having a diameter of 10 nm are formed, and when a second MOF is heat-treated, pores having a diameter of 100 nm are formed. When a nanostructure is prepared by mixing each of the first and second MOFs at 1:1, pores having a diameter of 10 nm and pores having a diameter of 100 nm are present at 1:1 in the prepared nanostructure. In the case of a nanostructure prepared by the above-described method, pores having different sizes are randomly disposed, as in FIG. 5A.

For another example, after the first MOF is laminated on a substrate, a heat treatment may be carried out by laminating the second MOF on the first MOF. When a nanostructure is prepared by the method, the nanostructure is composed of a plurality of layers. Among the layers, pores included in one layer has a diameter of 10 nm, and pores included in the other layer has a diameter of 100 nm. In the case of a nanostructure prepared by the above-described method, pores having different sizes are disposed in different layers, as in FIG. 5B.

Meanwhile, as in FIG. 5C, nanostructures 200a to 200c including only pores belonging to the same group may be prepared, and the sizes of the pores included in each of the nanostructures may be different from each other.

As described above, when MOFs having different sizes are used, the size distribution of pores included in the nanostructure may be adjusted.

Meanwhile, the nanostructure may be prepared by other preparation methods for preparing a porous structure without being limited to a method for preparing a nanostructure by using the MOF. For example, a method for preparing a nanostructure may be used by a method for forming a template using a surfactant.

Finally, a step of attaching an electrochromic material to the surface of the nanostructure is performed by immersing the nanostructure in a solution of the electrochromic material.

The electrochromic material may be the compound represented by Chemical Formulae 1 to 3, and is not limited thereto.

Meanwhile, different electrochromic materials may be attached to the nanostructure by sequentially immersing the nanostructure in different electrochromic solutions. Specifically, first and second electrochromic materials may be attached to the nanostructure by immersing the nanostructure in a solution of a first electrochromic material, and then immersing the nanostructure in a solution of a second electrochromic material having a molecular weight smaller than that of the first electrochromic material.

Here, it is preferred that the immersion in the solutions of different electrochromic materials is performed in descending order of molecular weight of the electrochromic material. Specifically, since the first electrochromic material has a molecular weight larger than that of the second electrochromic material, it is preferred that the immersion in the first electrochromic material is first carried out. Through this, it is possible to prevent an electrochromic material having a small molecular weight from being attached to a position to which an electrochromic material having a large molecular weight should be attached.

For example, the first electrochromic material may be selectively attached to pores having a relatively large diameter by immersing the nanostructure described in FIG. 5A in the solution of the first electrochromic material. Thereafter, the second electrochromic material may be attached to pores having a relatively small diameter by immersing the nanostructure in the solution of the second electrochromic material.

For another example, the first electrochromic material may be attached to only pores formed in a specific layer by immersing the nanostructure described in FIG. 5B in the solution of the first electrochromic material. Thereafter, the second electrochromic material may be attached to pores formed in a layer different from a layer to which the first electrochromic material is attached by immersing the nanostructure in the solution of the second electrochromic material.

The above-described method enables an electrochromic material having a large molecular weight and an electrochromic material having a small molecular weight to be bonded to pores having a relatively large diameter and pores and pores having a relatively small diameter, respectively.

Meanwhile, after different electrochromic material are attached to each of the nanostructures described in FIG. 5c, the nanostructures may be disposed in one electrochromic device.

It is obvious to the person skilled in the art that the present invention can be embodied in other specific forms without departing from the spirit and essential characteristics of the present invention.

Further, the aforementioned detailed description should not be interpreted as limitative in all aspects, and should be considered as illustrative. The scope of the present invention should be defined by the reasonable interpretation of the accompanying claims, and all the modifications within the equivalent scope of the present invention are included in the scope of the present invention.

The invention claimed is:

1. An electrochromic structure comprising:
   a rectangular cuboid nanostructure for an electrochromic layer, the rectangular cuboid nanostructure having a structure comprising nanopores; and
   electrochromic materials attached to surfaces of the rectangular cuboid nanostructure,
   wherein the rectangular cuboid nanostructure includes:
      a first layer having first pores of a first size, and a first electrochromic material of a first color attached to the first pores;
      a second layer having second pores of a second size smaller than the first size, and a second electrochromic material of a second color different from the first color and attached to the second pores; and
      a third layer having third pores of a third size smaller than the second size, and a third electrochromic material of a third color different from the first and second colors and attached to the third pores, wherein an upper surface of the second layer directly contacts a lower surface of the first layer, and a lower surface of the second layer directly contacts an upper surface of the third layer, wherein side surfaces of the first, second and third layers form one side surface of the rectangular cuboid nanostructure, and the one side surface of the rectangular cuboid nanostructure includes the first, second and third pores, and wherein the first electrochromic material has a larger diameter than the second electrochromic material.

2. The electrochromic structure of claim 1, wherein the rectangular cuboid nanostructure comprises a metal oxide.

3. The electrochromic structure of claim 1, wherein the first electrochromic material has a molecular weight different from that of the second electrochromic material.

4. The electrochromic structure of claim 1, wherein the electrochromic material taking on the blue color is represented by the following Formula 1, the electrochromic material taking on the red color is represented by the following Formula 2, and the electrochromic material taking on the green color is represented by the following Formula 3:

rectangular cuboid nanostructure in one or more solutions including one or more of the electrochromic materials, wherein the preparing the rectangular cuboid nanostructure comprises:
mixing metal organic frameworks having different sizes at a predetermined ratio; and
preparing pores in the rectangular cuboid nanostructure having different sizes by heat-treating the metal organic frameworks mixed at the predetermined ratio, wherein the rectangular cuboid nanostructure includes:
a first layer having first pores of a first size, and a first electrochromic material of a first color attached to the first pores;
a second layer having second pores of a second size smaller than the first size, and a second electrochromic material of a second color different from the first color and attached to the second pores; and
a third layer having third pores of a third size smaller than the second size, and a third electrochromic material of a third color different from the first and second colors and attached to the third pores,

[Formula 1]

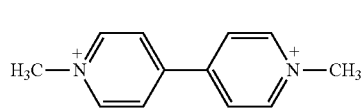

[Formula 2]

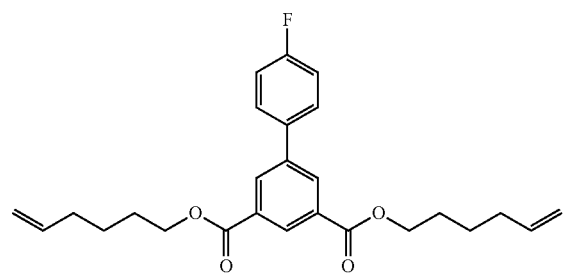

[Fomrula 3]

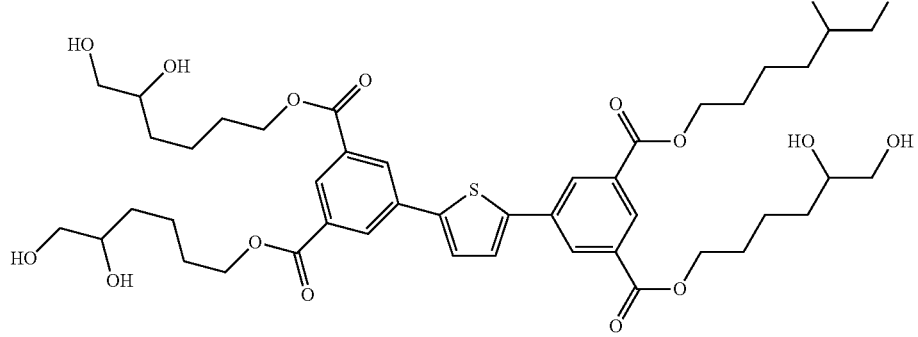

5. The electrochromic structure of claim 1, wherein the first layer is laminated and formed on the second layer.

6. The electrochromic structure of claim 1, wherein the first layer and the second layer are disposed in parallel.

7. A method for preparing an electrochromic nanostructure, the method comprising:
preparing a metal organic framework having a predetermined size;
preparing a rectangular cuboid nanostructure for an electrochromic layer, the rectangular cuboid nanostructure having a structure comprising nanopores by heat-treating the metal organic framework having the predetermined size; and
attaching electrochromic materials to surfaces of the rectangular cuboid nanostructure by immersing the wherein an upper surface of the second layer directly contacts a lower surface of the first layer, and a lower surface of the second layer directly contacts an upper surface of the third layer, wherein side surfaces of the first, second and third layers form one side surface of the rectangular cuboid nanostructure, and the one side surface of the rectangular cuboid nanostructure includes the first, second and third pores, and wherein the first electrochromic material has a larger diameter than the second electrochromic material.

8. The method of claim 7, wherein the attaching of the electrochromic materials to the surfaces of the rectangular cuboid nanostructure comprises:

attaching the first electrochromic material to the surfaces of the rectangular cuboid nanostructure by immersing the rectangular cuboid nanostructure in a solution of the first electrochromic material; and attaching the second electrochromic material to the surfaces of the rectangular cuboid nanostructure by immersing the rectangular cuboid nanostructure in a solution of the second electrochromic material while the first electrochromic material is attached to the surfaces of the rectangular cuboid nanostructure, and the second electrochromic material has a molecular weight smaller than that of the first electrochromic material.

9. The method of claim 7, wherein the preparing of the rectangular cuboid nanostructure comprises:

laminating a first metal organic framework to a predetermined thickness;

laminating a second metal organic framework to a predetermined thickness on the laminated first metal organic framework; and preparing a nanostructure comprising pores having different sizes by heat-treating the first and second metal organic frameworks.

10. The method of claim 7, wherein the preparing of the rectangular cuboid nanostructure comprises:

laminating a first metal organic framework to a predetermined thickness;

laminating a second metal organic framework to the predetermined thickness in parallel with the laminated first metal organic framework; and preparing a nanostructure comprising pores having different sizes by heat-treating the first and second metal organic frameworks.

11. An electrochromic device comprising:

a first transparent electrode and a second transparent electrode;

an ion storage layer;

an electrochromic layer; and an electrolyte layer disposed between the ion storage layer and the electrochromic layer, wherein the electrochromic layer includes a rectangular cuboid nanostructure having a structure comprising nanopores, and electrochromic materials attached to surfaces of the rectangular cuboid nanostructure, wherein the rectangular cuboid nanostructure includes:

a first layer having first pores of a first size, and a first electrochromic material of a first color attached to the first pores;

a second layer having second pores of a second size smaller than the first size, and a second electrochromic material of a second color different from the first color and attached to the second pores; and a third layer having third pores of a third size smaller than the second size, and a third electrochromic material of a third color different from the first and second colors and attached to the third pores, wherein an upper surface of the second layer directly contacts a lower surface of the first layer, and a lower surface of the second layer directly contacts an upper surface of the third layer, wherein side surfaces of the first, second and third layers form one side surface of the rectangular cuboid nanostructure, and the one side surface of the rectangular cuboid nanostructure includes the first, second and third pores, and wherein the first electrochromic material has a larger diameter than the second electrochromic material.

12. The electrochromic device of claim 11, wherein the first and second pores are disposed on at least three outer surfaces of the rectangular cuboid.

13. The electrochromic device of claim 11, wherein the electrochromic materials are configured to be oxidized or reduced between the first and second transparent electrodes by transferring electric charge to the electrochromic layer.

14. The electrochromic device of claim 11, wherein the electrochromic layer has a small thickness that is less than a thickness of the electrolyte layer.

* * * * *